(12) United States Patent
Kato (10) Patent No.: US 8,397,339 B2
(45) Date of Patent: Mar. 19, 2013

(54) REFERENCE MEMBER CLEANING DEVICE, AND REFERENCE MEMBER CLEANING METHOD

(75) Inventor: Takuji Kato, Ichikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 156 days.

(21) Appl. No.: 13/085,874

(22) Filed: Apr. 13, 2011

(65) Prior Publication Data

US 2011/0185530 A1 Aug. 4, 2011

Related U.S. Application Data

(63) Continuation of application No. PCT/JP2009/067800, filed on Oct. 14, 2009.

(30) Foreign Application Priority Data

Oct. 14, 2008 (JP) ................................. 2008-264940

(51) Int. Cl.
*G07D 7/00* (2006.01)

(52) U.S. Cl. .............. 15/250.001; 15/250.22; 15/250.04

(58) Field of Classification Search ............. 15/250.001, 15/250.04, 250.22
See application file for complete search history.

(56) References Cited

FOREIGN PATENT DOCUMENTS

| JP | 58-158656 | 9/1983 |
| JP | 03-245023 | 10/1991 |
| JP | 9-506200 | 6/1997 |
| JP | 2007-279896 | 10/2007 |

OTHER PUBLICATIONS

International Search Report for PCT/JP2009/067800.

*Primary Examiner* — Shay Karls
(74) *Attorney, Agent, or Firm* — Pillsbury Winthrop Shaw Pittman, LLP (57) ABSTRACT

According to one embodiment, a reference member cleaning device used in an optical detection unit causes a driving module to convey a reference member and to rotate a wipe-off member. The reference member cleaning device of the optical detection unit transmits the power of the driving module to both the wipe-off member and the reference member, in such a manner that the rotating direction of the wipe-off member and the conveying direction of the reference member are reversed at the position where the wipe-off member and the reference member come into contact with each other.

9 Claims, 6 Drawing Sheets

REFERENCE MEMBER CLEANING DEVICE, AND REFERENCE MEMBER CLEANING METHOD

CROSS-REFERENCE TO RELATED APPLICATIONS

This is a Continuation Application of PCT Application No. PCT/JP2009/067800, filed Oct. 14, 2009, which was published under PCT Article 21(2) in Japanese.

This application is based upon and claims the benefit of priority from Japanese Patent Application No. 2008-264940, filed Oct. 14, 2008; the entire contents of which are incorporated herein by reference.

FIELD

Embodiments described herein relate generally to a reference member cleaning device in an optical detection unit, which detects light from a conveyed sheet, and a reference member cleaning method, for example.

BACKGROUND

A sheet processing apparatus configured to count and discriminate a variety of paper sheets has been practically used. A sheet processing apparatus takes in sheets one by one from an input module, and conveys them to an optical detection unit. An optical detection unit detects light from a sheet, and obtains an image based on the detected light. A sheet processing apparatus determines denomination, authentication, and possibility of recirculation of a sheet, based on the obtained image. A sheet processing apparatus assorts and stacks a sheet, based on the results of determination.

An illuminator to emit light to a sheet is deteriorated in light intensity over time. When the light intensity of an illuminator is deteriorated, an image obtained by an optical detection unit may be darkened.

Therefore, an optical detection unit is provided with an illuminator, a detector, and a standard reflector. An illuminator emits light in a predetermined area (a detection surface). A detector detects light from a detection surface, and obtains an image. A standard reflector (a reference member) applies reference light to the detector.

When a sheet is present on a detection surface, light emitted from an illuminator is reflected on the sheet. The light reflected on the sheet enters a detector. The detector obtains an image of the sheet by the incident light.

When a sheet does not present on a detection surface, light emitted from an illuminator is reflected on a reference member. The light reflected on the reference member (a reference light) enters a detector. Therefore, the detector obtains a reference light.

An optical detection unit corrects the gain of a signal detected by a detector based on a reference light detected by a reference member. An optical detection unit obtains an image of a sheet by the detector, which corrects the signal gain. Therefore, an optical detection unit can obtain a stable image of a sheet.

However, when a sheet is processed, dust and stains may be adhered to a reference member. In this case, a reference light detected by a detector from a reference member may fluctuate. In other words, a signal may not be exactly corrected, and a stable image may not be obtained by the detector. To solve this problem, it is necessary to remove dust and stains from a reference member.

For example, Japanese Patent Document 1 discloses a method of removing stains by providing felt or the like at a position to contact a reference member when the reference member is taken out.

DETAILED DESCRIPTION

In general, according to one embodiment, a reference member cleaning device used in an optical detection unit, comprises: a reference member which reflects light; a wipe-off member which is provided at a position to contact the reference member, rotatable forward and backward, and cleans a surface of the reference member; a drive module which generates power in a forward or backward rotating direction; a transmission module which is connected to a rotating shaft of the drive module, transmits the power of the drive module to the reference member to convey the reference member in a predetermined direction, and transmits the power of the drive module to the wipe-off member to rotate the wipe-off member in a predetermined direction; and a control module which controls the rotating direction of the drive module.

Hereinafter, an explanation will be given of a reference member cleaning device and reference member cleaning method according to an embodiment of the invention with reference to the accompanying drawings.

Figure 1:
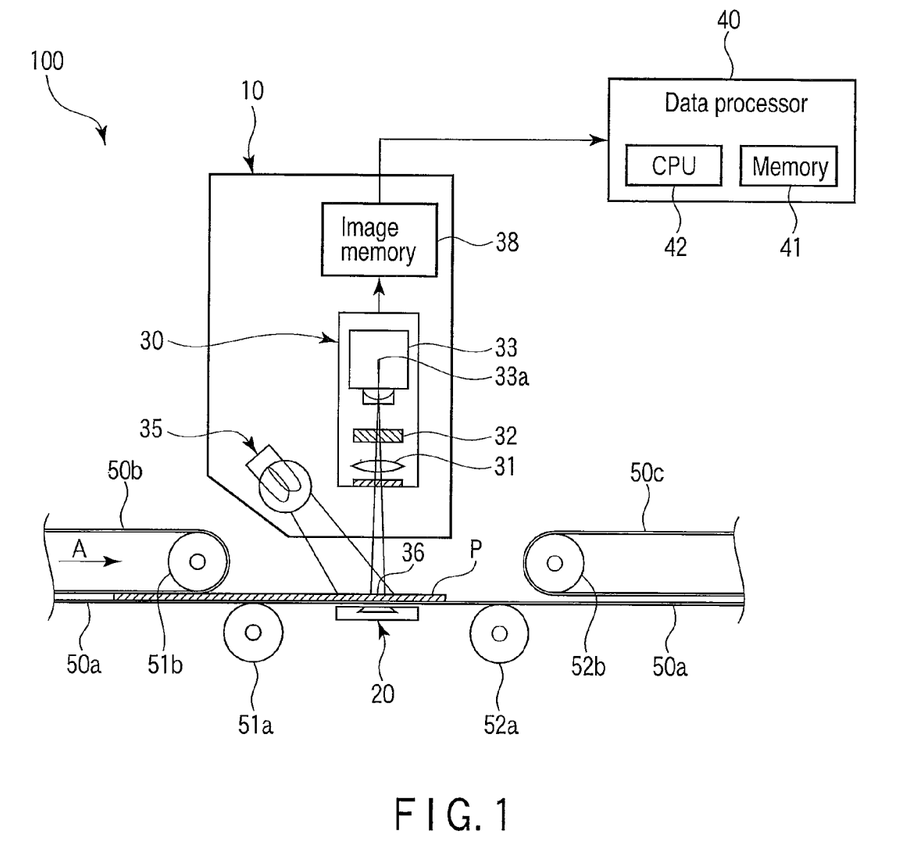
FIG. 1 is a diagram for explaining a configuration of an optical detection unit according to an embodiment of the invention.

FIG. 1 is a diagram for explaining a configuration of an optical detection unit 10 according to an embodiment of the invention.

The optical detection unit 10 is placed close to a conveying path 50 of a sheet processing apparatus 100, for example. The optical detection unit 10 comprises a standard reflector (reference member) 20, a detector 30, a lamp 35, and an image memory 38.

The conveying path 50 is a conveying system to convey a sheet P to be processed by the sheet processing apparatus 100. The conveying path 50 comprises conveying rollers 51a, 51b, 52a and 52b, and conveying belts 50a, 50b and 50c.

The conveying rollers are driven and rotated by a not-shown motor. The conveying belts are moved by the conveying rollers. In other words, when the conveying rollers are rotated, the conveying belts looped tightly over the conveying rollers are moved in a predetermined direction. The conveying belts hold a sheet P as a detected medium, and move it in the direction of the arrow A.

In this embodiment, the conveying rollers and conveying belts are arranged not to pass within a detection area of the detector 30, so that an image of a sheet P can be obtained by the optical detection unit 10.

The lamp 35 functions as an illuminator. The lamp 35 emits light to a detection surface 36, which includes at least the detection area of the detector 30. When a sheet P is present on the detection surface 36, the light emitted from the lamp 35 is reflected on the sheet P. When a sheet P is not present on the detection surface 36, the light emitted from the lamp 35 is reflected on the standard reflector 20.

The lamp 35 is an illuminator, for example, a halogen lamp or an ultraviolet-ray lamp. A wavelength of the lamp 35 is set depending on the pattern printed on a sheet P to detect, and the properties of ink used. A filter to transmit only light of a predetermined wavelength may be provided between the lamp 35 and the detection surface 36.

The standard reflector 20 is placed opposite to the detector 30 across the conveying belt 50, as shown in FIG. 1. The standard reflector 20 has a standard reflection surface as described later. The standard reflection surface reflects the light emitted from the lamp 35, and applies reference light to the detector 30. In other words, the standard reflection surface reflects incident light as reference light. The standard reflector 20 is supported by a standard reflector cleaning device (a reference member cleaning device) as described later.

The detector 30 comprises a lens 31, a filter 32, and a camera 33. The lens 31 condenses the light reflected from the sheet P or standard reflector 20. The filter 32 transmits only the light with a predetermined wavelength among the light condensed by the lens 31. The camera 33 detects the light transmitted through the filter 32.

The camera 33 is provided with a line image sensor 33a. The line image sensor 33a comprises a plurality of light-emitting elements, for example a charge coupled device (CCD), aligned in the direction (the scanning direction) orthogonal to the direction of conveying a sheet P. The line image sensor 33a continuously obtains an image of the detection surface 36, and sequentially outputs the image to the image memory 38. Thereby, the line image sensor obtains a whole image of a sheet P.

The image memory 38 combines and stores images corresponding to one line output from the detector 30. In other words, the image memory 38 generates a whole image of a sheet P by images corresponding to a plurality of lines output from the detector 30.

A data processor 40 is a microcomputer system, for example. The data processor 40 comprises a memory 41, and a central processing unit (CPU) 42. The CPU 42 reads an image of a sheet P from the image memory 38 of the optical detection unit 10. The CPU 42 stores the read image in the memory 41. The CPU 42 processes various data stored in the memory 41.

Figure 2:
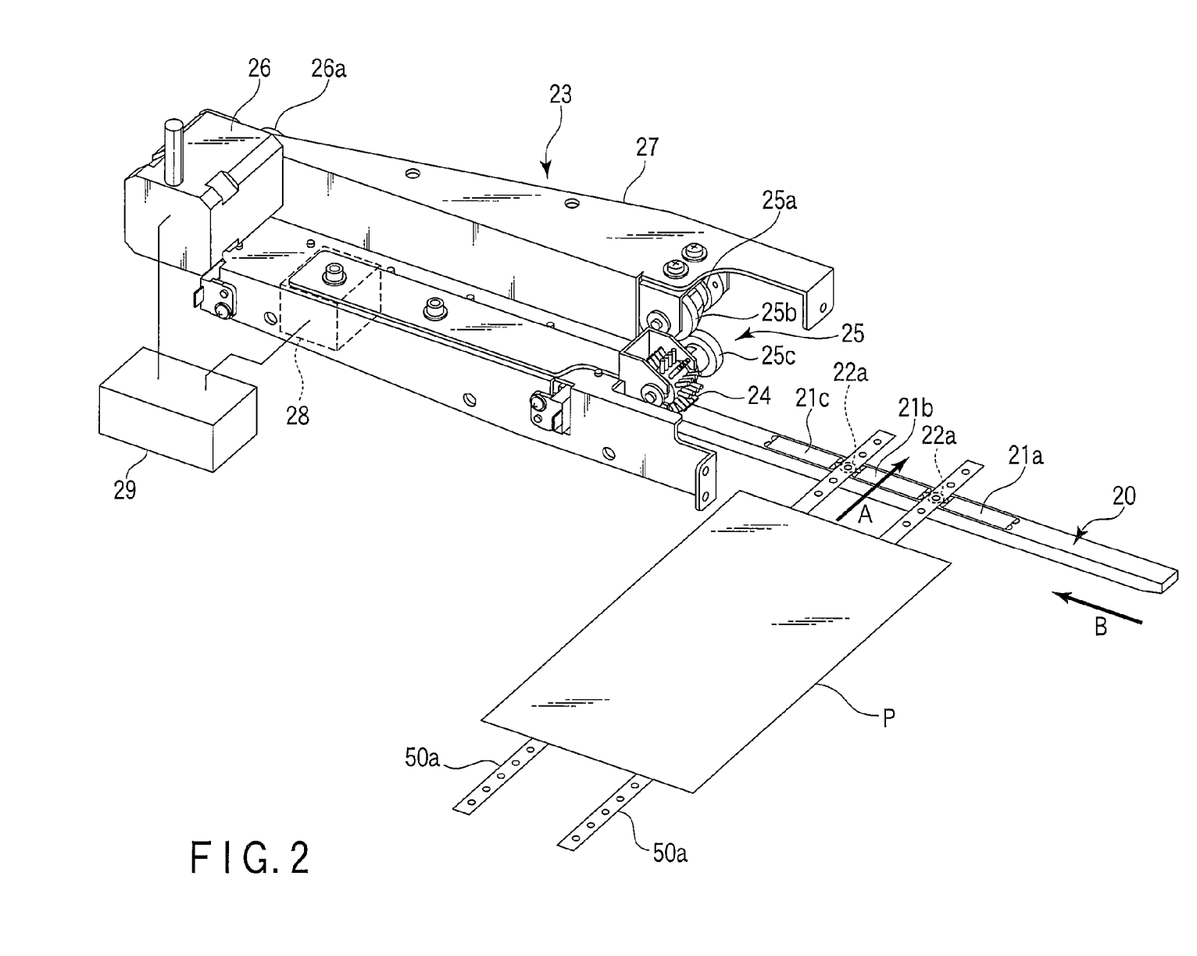
FIG. 2 is a diagram for explaining a configuration of a reference member cleaning device used in the optical detection unit shown in FIG. 1.

FIG. 2 is a diagram for explaining a configuration of a standard reflector cleaning device 23 used in the optical detection unit shown in FIG. 1.

The standard reflector cleaning device 23 supports the standard reflector 20. The standard reflector 20 is placed opposite to the cleaning device 23 across a conveyed sheet P and the conveying belt 50a. The standard reflector 20 has standard reflection surfaces 21a, 21b and 21c. Each of the standard reflection surfaces 21a, 21b and 21c is provided on the surface of the standard reflector 20 close to the detector 30.

The optical detection unit 10 is preferably configured to read the whole surface of a sheet P. However, when a sheet P is conveyed in being held by the conveying belt 50, a certain area of the detection surface 36 is interrupted by the conveying belt 50. To prevent it, in this embodiment, the lower side of a sheet P is absorbed by the conveying belt 50a on the detection surface 36.

For this purpose, the standard reflector 20 has a hole 22a. The hole 22a is an air vent hole. The standard reflector 20 is provided under the conveying belt 50a conveying a sheet P. The hole 22a is provided in a part on which the conveying belt 50a passes. Therefore, the standard reflection surfaces 21a to 21c are placed in three areas separated by the conveying belt 50a.

Further, as shown in the drawing, the conveying belt 50a itself has a hole. Therefore, when air is vent from the hole 22a, a sheet P is absorbed by the conveying belt 50a. As a result, the sheet P can be conveyed in a state without shielding between the sheet P and the detector 30.

The standard reflector cleaning device 23 comprises a rotary brush 24, a transmission module 25, a drive motor 26, a guide member 27, and a position detector sensor 28. The standard reflector cleaning device 23 further comprises a control unit 29 to control the above constituent parts. The standard reflector cleaning device 23 is configured to move the standard reflector 20 forward and backward in the direction of the arrow B, namely in the direction orthogonal to the sheet P conveying direction (indicated by the arrow A) by the motor 26 and transmission module 25.

The rotary brush 24 is a cleaning member rotatable forward and backward about a shaft. The rotary brush 24 is provided at a position to slidingly contact the standard reflector 20. The rotary brush 24 has the width equal to or larger than the standard reflector 20. The cleaning member may be any thing capable of removing dust and stains without damaging the standard reflection surfaces 21a to 21c.

The transmission module 25 transmits the power of the drive motor 26 to each part. The transmission module 25 comprises rotary elements such as a pulley 25a, and gears 25b and 25c. The drive motor 26 is a module to generate power in the forward or backward direction. The guide member 27 supports the shafts of the drive motor 26 and transmission module 25. The position detector sensor 28 monitors movement of the standard reflector 20.

Next, an explanation will be given of the operation to move the standard reflector 20.

Figure 3:
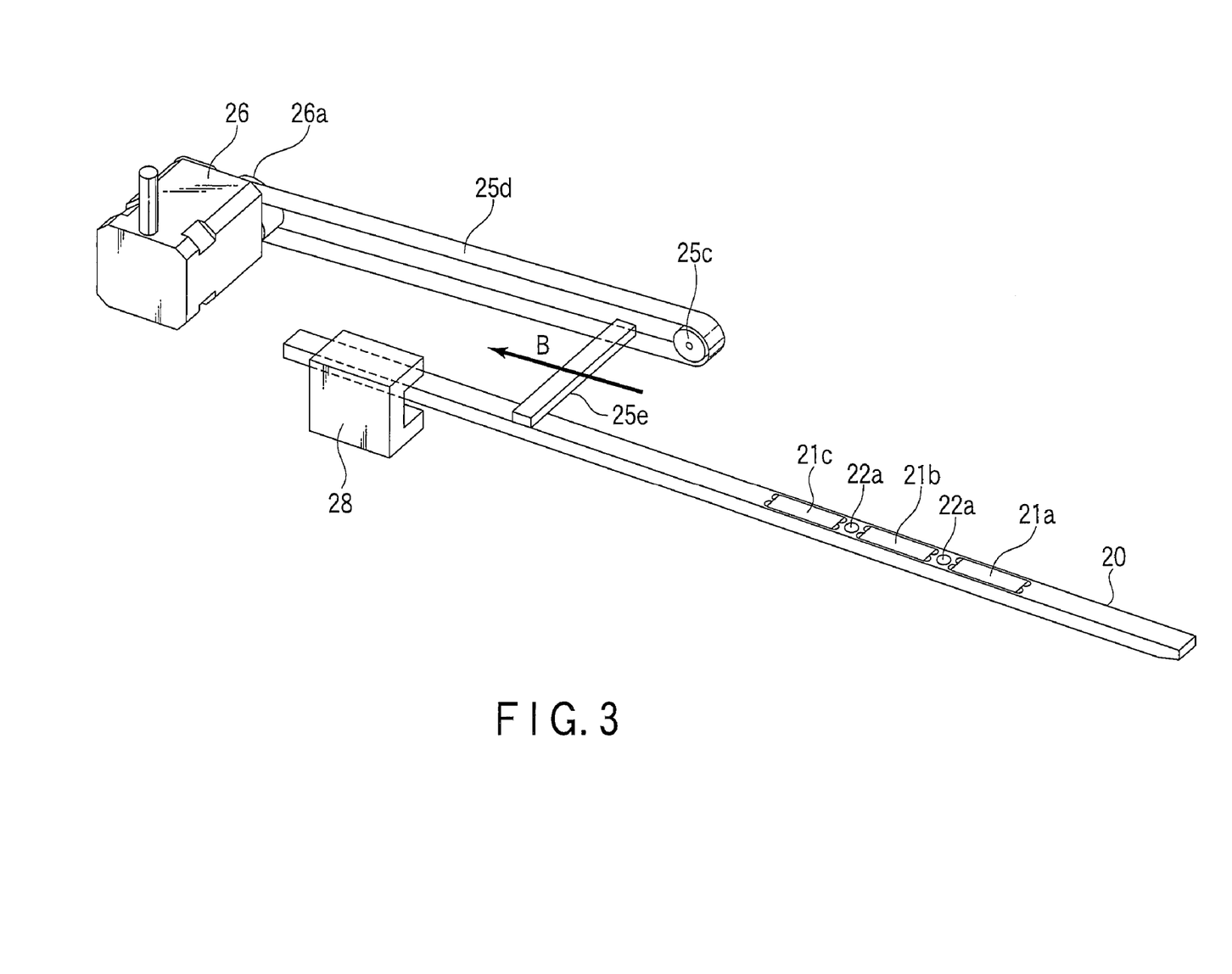
FIG. 3 is a diagram for explaining a configuration of the reference member cleaning device shown in FIG. 2.

As shown in FIG. 3, the transmission module 25 further comprises a drive belt 25d, and an interlock member 25e.

The drive belt 25d is wound around the pulley 25a and the pulley 26a connected to the shaft of the drive motor 26. In other words, the pulley 25a is rotated in the same direction as the rotation of the drive motor 26.

The drive belt 25d is moved in a predetermined direction by the drive motor 26. The drive motor 26 can be rotated forward and backward. Therefore, the drive belt 25d can be moved in the opposite direction by the drive motor 26. In other words, the drive belt 25d is moved in the direction of the arrow B by the drive motor 26. The pulleys 26a and 25a are placed with space at least farther than the moving distance of the standard reflector 20.

The interlock member 25e connects the drive belt 25d and standard reflector 20. One end of the interlock member 25e is connected to the drive belt 25d, and the other end is connected to the standard reflector 20.

In other words, when the drive motor 26 is rotated forward, the drive belt 25d moves the interlock member 25e and standard reflector 20 in the direction of the arrow B. When the drive motor 26 is rotated backward, the drive belt 25d moves the interlock member 25e and standard reflector 20 in the direction opposite to the arrow B. Therefore, the standard reflector cleaning device 23 can move the standard reflector 20 forward and backward.

Figure 4:
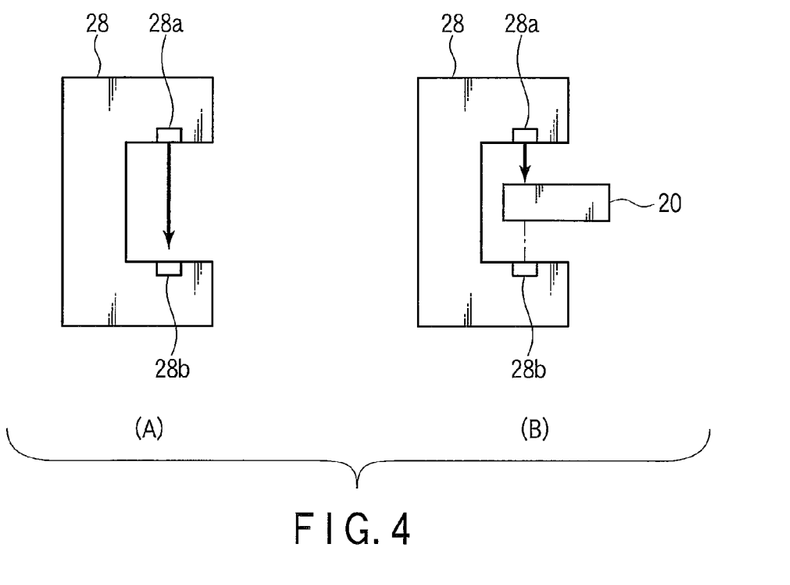
FIG. 4 is a diagram for explaining a configuration of a position detector sensor shown in FIG. 2 and FIG. 3.

FIG. 4 is a diagram for explaining a configuration of the position detector sensor 28 shown in FIGS. 2 and 3.

The position detector sensor 28 detects the moving distance of the standard reflector 20 by detecting infrared radiation, for example.

The position detector sensor 28 comprises an emitter 28a, and a receptor 28b. The emitter 28a emits light, for example infrared rays. The receptor 28b detects the emitted light. The emitter 28a and receptor 28b are provided opposite to each other, as shown in FIG. 4.

(A) in FIG. 4 shows a case where the standard reflector 20 is not present between the emitter 28a and receptor 28a. (B) in FIG. 4 shows a case where the standard reflector 20 is present between the emitter 28a and receptor 28a.

As shown in (A) in FIG. 4, when the standard reflector 20 is not present between the emitter 28a and receptor 28b, the infrared ray emitted from the emitter 28a enters the receptor 28b. In this case, the receptor 28b sends a signal indicating the presence of the standard reflector 20 between the emitter 28a and receptor 28b.

As shown in (B) in FIG. 4, when the standard reflector 20 is present between the emitter 28a and receptor 28b, the infrared ray emitted from the emitter 28a is interrupted by the standard reflector 20, and does not enter the receptor 28b. The control unit 29 determines whether the standard reflector 20 is present between the emitter 28a and receptor 28b of the position detector sensor 28, based on the signal output from the position detector sensor 28.

When the control unit 29 determines that the standard reflector 20 is present between the emitter 28a and receptor 28b of the position detector sensor 28, the control unit controls the drive motor 26 to rotate backward. By adjusting the position and number of the position detector sensor 28, the standard reflector cleaning device 23 can move the standard reflector 20 to a predetermined position.

Figure 5:
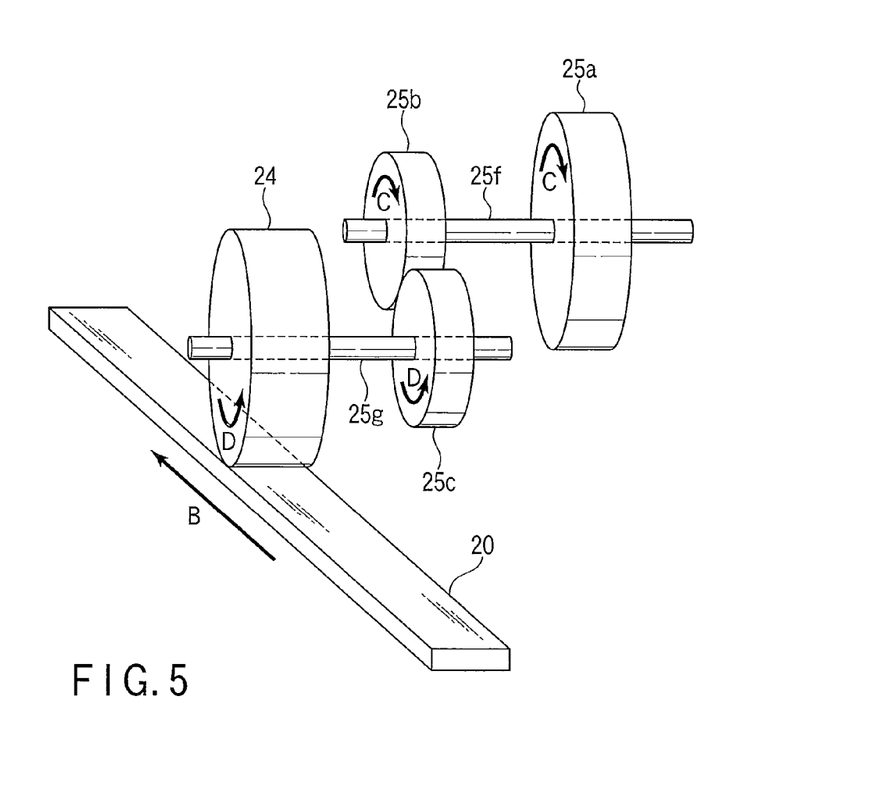
FIG. 5 is a diagram for explaining a configuration of the reference member cleaning device shown in FIG. 2.

FIG. 5 is a diagram for explaining a configuration of the transmission module 25 of the reference member cleaning device 23.

As described above, the drive belt 25d is wound around the pulleys 26a and 25a. Therefore, the pulley 25a is rotated interlocking with the drive motor 26.

As shown in FIG. 5, the transmission module 25 further comprises rotary shafts such as shafts 25f and 25g. The shafts 25f and 25g are supported by the guide member 27 shown in FIG. 2.

The shaft 25f is provided with the pulley 25a and gear 25b. When the pulley 25a is rotated by the drive motor 26, the shaft 25f is rotated interlocking with the pulley 25a. When the shaft 25f is rotated, the gear 25b is rotated interlocking with the shaft 25f.

The shaft 25g is provided with the gear 25c and rotary brush 24. The gear 25c is placed at a position to engage with the gear 25b. In other words, when the gear 25b is rotated, the gear 25c is rotated in the direction opposite to the rotation of the gear 25b.

When the gear 25c is rotated by the gear 25b, the shaft 25g is rotated interlocking with the gear 25c. When the shaft 25g is rotated, the rotary brush 24 is rotated interlocking with the shaft 25g.

As explained in FIG. 3, when the standard reflector 20 is moved in the direction of the arrow B, the pulley 25a is rotated in the direction of the arrow C (clockwise). The gear 25b is rotated in the direction of the arrow C interlocking with the pulley 25a.

The gear 25b transmits the rotation in the direction of the arrow D (counterclockwise) to the gear 25c. The rotary brush 24 is rotated in the direction of the arrow D interlocking with the gear 25c.

Figure 6:
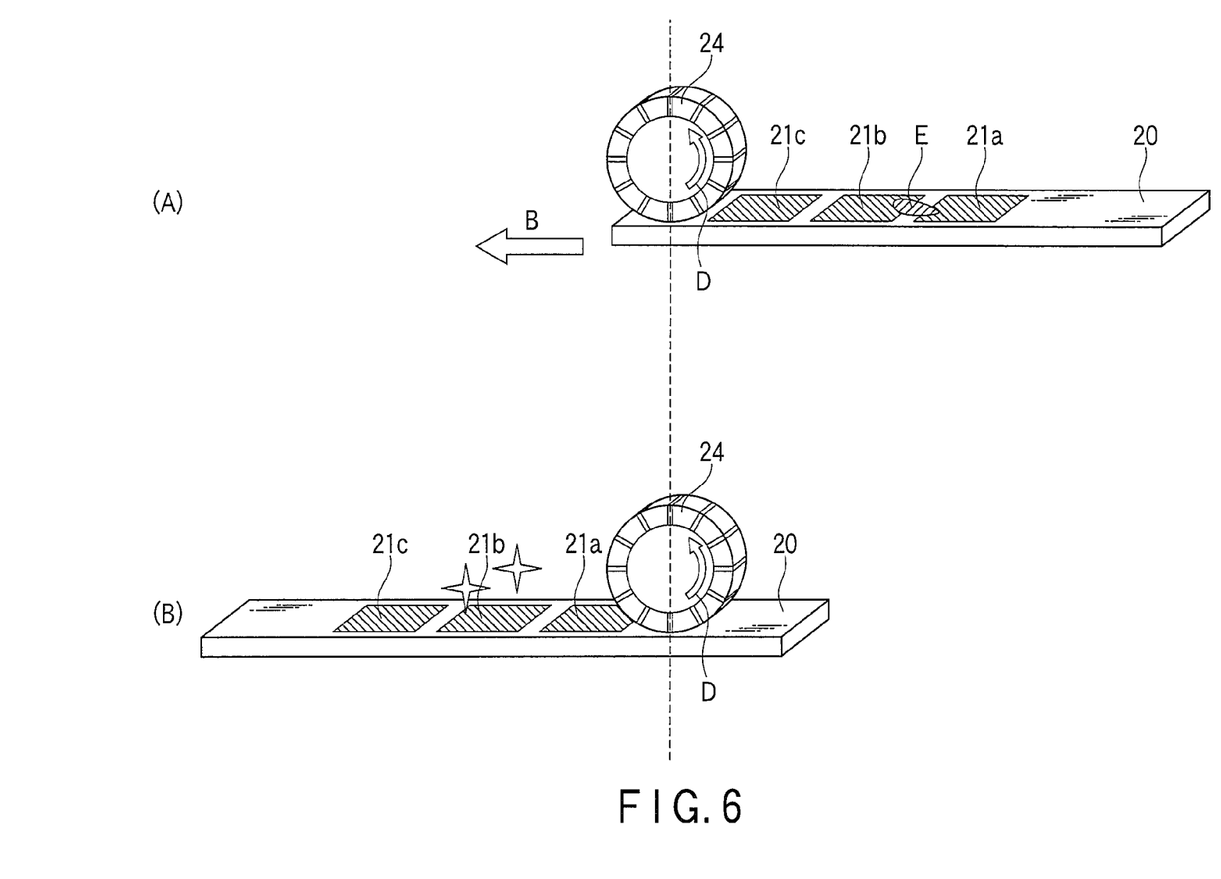
FIG. 6 is a diagram for explaining operations of the reference member cleaning device shown in FIG. 2.

FIG. 6 is a diagram for explaining the operation of the reference member cleaning device 23.

As shown in (A) in FIG. 6, the standard reflector cleaning device 23 receives a request to clean the standard reflector 20 from the sheet processing apparatus 100, and cleans a stain E on the standard reflector 20 (standard reflector cleaning).

When cleaning the standard reflector, the standard reflector cleaning device 23 rotates the drive motor 26 forward until the position detector sensor 28 detects that the standard reflector 20 is moved by a predetermined distance. In this case, the standard reflector 20 is moved by a predetermined distance in the direction of the arrow B shown in FIG. 5. In other words, the standard reflector cleaning device 23 pull the standard reflector 20 in the direction of the arrow B.

The rotary brush 24 is rotated in the direction of the arrow D shown in FIG. 5. The rotary brush 24 is provided at a position to slidingly contact the standard reflector 20. Therefore, the rotary brush 24 can wipe off dust and stains on the standard reflector 20 moving in the direction of the arrow B. In other words, the rotary brush 24 cleans the whole surface of the standard reflector 20 by rotating in the direction opposite to the standard reflector 20 being pulled in.

As a result, the standard reflector 20 is pulled in up to the position shown in (B) in FIG. 6. The standard reflector cleaning device 23 can remove the stain E on the standard reflector 20.

When the position detector sensor 28 detects that the standard reflector 20 has been moved by a predetermined distance, the standard reflector cleaning device 23 rotates the drive motor 26 backward. In this case, the standard reflector 20 is moved by a predetermined distance in the direction opposite to the arrow B shown in FIG. 5. Therefore, the standard reflector cleaning device 23 pushes the standard reflector 20 to the original position (home position).

Further, in this case, the rotary brush 24 is rotated in the direction opposite to the arrow D shown in FIG. 5. Therefore, the rotary brush 23 can wipe off again the dust and stain on the standard reflector 20 being moved in the direction opposite to the arrow B.

As described above, the standard reflector cleaning device 23 according to the embodiment can move the standard reflector 20 in a predetermined direction, simultaneously with rotating the rotary brush 24 provided at a position to slidingly contact the standard reflector 20, by driving one drive motor 26. Further, the standard reflector cleaning device 23 can move the standard reflector 20 and rotary brush 24, so that the rotating direction of the rotary brush is reversed to the moving direction of the standard reflector, at the position to slidingly contact the standard reflector.

As a result, the standard reflector 20 can be automatically cleaned, while it is manually cleaned in the prior art. Therefore, it is possible to provide a reference member cleaning device and a reference member cleaning method, which can efficiently clean the reference member.

In the embodiment described herein, the position detector sensor 28 detects the position of the standard reflector 20. The embodiment is not limited to this configuration. For example, the position of the standard reflector 20 may be detected by the number of revolutions of the drive motor 26. In this case, the control unit 29 rotates the drive motor 26 forward by a predetermined number, and then controls the motor to rotate backward by a predetermined number.

Figure 7:
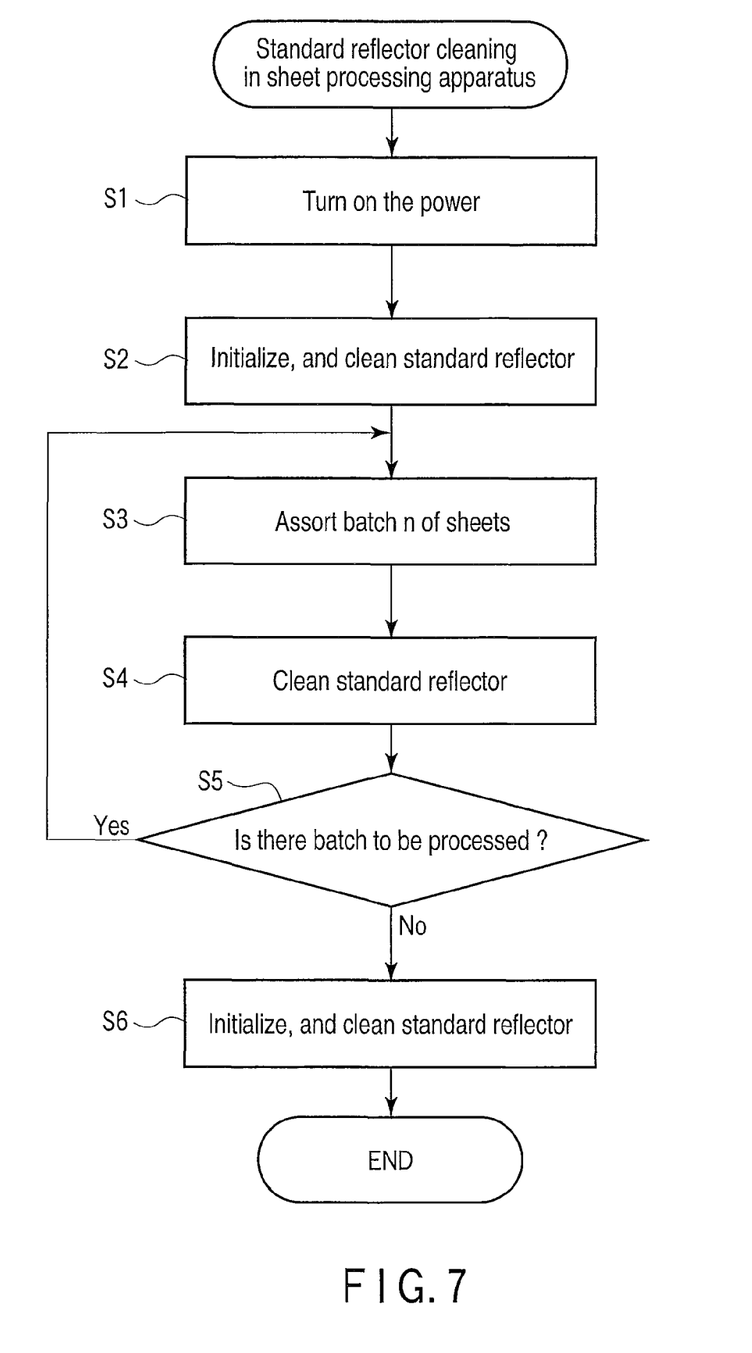
FIG. 7 is a flowchart of operations of a sheet processing apparatus shown in FIG. 1.

FIG. 7 is a flowchart for explaining the operation of the sheet processing apparatus 100 shown in FIG. 1.

When the power is turned on (step S1), the sheet processing apparatus 100 is initialized, and cleans the standard reflector (step S2). When the sheet processing apparatus 100 is initialized, each mechanism is returned to a home position.

Then, the sheet processing apparatus 100 sends a standard reflector cleaning request to the standard reflector cleaning device 23 of the optical detection unit 10. The standard reflector cleaning device 23 receives the cleaning request, and cleans the standard reflector.

The sheet processing apparatus 100 assorts the sheet P stacked in a batch (step S3). In other words, the sheet processing apparatus 100 takes in the sheet P of the batch one by one, and inspects it by the optical detection unit 10 and other inspection devices. Therefore, the sheet processing apparatus 100 discriminates and authenticates the sheet P, and determines whether the sheet P is stained. Based on the results of discrimination, authentication and determination, the sheet P is assorted and stacked.

After assorting one batch, the sheet processing apparatus 100 cleans the standard reflector (step S4). In other words, the sheet processing apparatus 100 sends a standard reflector cleaning request to the standard reflector cleaning device 23 of the optical detection unit 10. The standard reflector cleaning device 23 receives the standard reflector cleaning request, and cleans the standard reflector as described above.

The sheet processing apparatus 100 determines whether a next batch is present (step S5). When a next batch is present (YES in step S5), the sheet processing apparatus 100 goes to step S3, and assorts the sheet P.

When a next batch is not present (NO in step S5), the sheet processing apparatus 100 is initialized, and cleans the standard reflector (step S6), and terminates the operation.

As described herein, the sheet processing apparatus 100 according to the embodiment cleans the standard reflector at the timing when the operation is started and completed, and when each batch processing is completed. Therefore, the sheet processing apparatus 100 can assort each batch by using a cleaned standard reflector.

Therefore, the optical detection unit 10 can prevent variations in the level of reference light obtained from the standard reflector 20 caused by dust and stains on the standard reflector 20. As a result, the optical detection unit 10 is prevented from misjudging the sheet P.

In the embodiments described herein, the standard reflector is cleaned at the timing when the operation is started and completed, and when each batch processing is completed. The cleaning timing is not limited to them. The standard reflector may be cleaned at the time when a predetermined input operation is performed in the operation input module of the sheet processing apparatus 100.

The invention is not limited to the embodiments described herein. The invention may be embodied in practical phases by modifying the constituent elements without departing from its spirit or essential characteristics. The invention may be embodied in other specific forms by appropriately combining the constituent elements disclosed herein. For example, some of the disclosed constituent elements may be deleted, or the constituent elements of different embodiments may be combined.

According to an aspect of the invention, there is provided a reference member cleaning device, and a reference member cleaning method, which are configured to efficiently clean a reference member.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A reference member cleaning device used in an optical detection unit, comprising:
    a reference member which reflects light;
    a wipe-off member which is provided at a position to contact the reference member, rotatable forward and backward, and cleans a surface of the reference member;
    a drive module which generates power in a forward or backward rotating direction;
    a transmission module which is connected to a rotating shaft of the drive module, transmits the power of the drive module to the reference member to convey the reference member in a predetermined direction, and transmits the power of the drive module to the wipe-off member to rotate the wipe-off member in a predetermined direction; and
    a control module which controls the rotating direction of the drive module.

2. The reference member cleaning device according to claim 1, wherein the transmission module transmits the power of the drive module, so that the conveying direction of the reference member is reversed to the rotating direction of the wipe-off member at a point to contact the reference member.

3. The reference member cleaning device according to claim 2, wherein the transmission module further comprising:
    a first rotary element;
    a belt which is wound around the rotating shaft of the drive module and the first rotary element; and
    an interlock member which interlocks the belt with the reference member.

4. The reference member cleaning device according to claim 3, wherein the transmission module further comprising:
    a first rotating shaft which is rotated interlocking with the first rotary element;
    a second rotary element which is rotated interlocking with the first rotating shaft;
    a third rotary element which is connected to the second rotary element, and is rotated in the direction opposite to the rotating direction of the second rotary element; and
    a second rotating shaft which is rotated interlocking with the third rotary element; and
    the wipe-off member is rotated interlocking with the second rotating shaft.

5. The reference member cleaning device according to claim 3, wherein the rotating shaft of the drive module and the first rotary element are placed with space at least farther than a distance to move the reference member.

6. The reference member cleaning device according to claim 2, further comprising a position detector sensor to detect the conveying distance of the reference member,
    wherein the control module controls the rotating direction of the drive module, based on the output of the position detector sensor.

7. The reference member cleaning device according to claim 6, wherein the control module changes the rotating direction of the drive module, when determining that the reference member has been conveyed over a predetermined distance, based on the output of the position sensor.

8. The reference member cleaning device according to claim 2, wherein the control module determines a conveying distance of the reference member, and changes the rotating direction of the drive module, when determining that the reference member has been conveyed over a predetermined distance, based on the number of revolutions of the drive module.

9. A reference member cleaning method used in a reference member cleaning device comprising a reference member to reflect light, and a wipe-off member to clean a surface of the reference member, comprising:

generating power in a forward or backward rotating direction;

transmitting the power to the reference member to convey the reference member in a predetermined direction, and transmitting the power to the wipe-off member to rotate the wipe-off member in a predetermined direction; and controlling the rotating direction of the power.

* * * * *